United States Patent
Crimaldi

(10) Patent No.: US 8,192,993 B1
(45) Date of Patent: *Jun. 5, 2012

(54) FORMULATIONS FOR IMPARTING TRACEABILITY AND/OR TRACKABILITY TO ONE OR MORE CHEMICALS

(76) Inventor: Joseph James Crimaldi, Avon, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/244,293

(22) Filed: Sep. 24, 2011

Related U.S. Application Data

(63) Continuation of application No. 12/629,005, filed on Dec. 1, 2009, now Pat. No. 8,053,240.

(60) Provisional application No. 61/200,571, filed on Dec. 1, 2008.

(51) Int. Cl.
*G01N 37/00* (2006.01)

(52) U.S. Cl. .................. 436/56; 8/506; 8/550; 8/636

(58) Field of Classification Search .................. None
See application file for complete search history.

(56) References Cited

OTHER PUBLICATIONS

Pepling, M. et al.; Use and Assessment of Marker Dyes used with Herbicides, 1997, USDA Order Nos. 43-3187-7-0408, Task No. 10. Anand Talc, retrieved from Internet http://web.archive.org/web/20021004023109/http://anandtalc.com/applications.html.

*Primary Examiner* — Yelena G. Gakh
*Assistant Examiner* — Robert Xu

(57) ABSTRACT

The invention relates to chemical formulations that can be used to render such chemicals easier to identify upon application to a surface. In one embodiment, the present invention relates to formulations designed to render herbicides, fungicides, pesticides, insecticides and/or phytotoxins easier to identify upon application to one or more types of vegetation. In another embodiment, the present invention relates to formulations designed to render water-soluble herbicides, fungicides, pesticides, insecticides and/or phytotoxins easier to identify upon application to one or more types of vegetation.

20 Claims, No Drawings

FORMULATIONS FOR IMPARTING TRACEABILITY AND/OR TRACKABILITY TO ONE OR MORE CHEMICALS

RELATED APPLICATION DATA

This application claims priority to and is a continuation of U.S. patent application Ser. No. 12/629,005 filed Dec. 1, 2009, which issued as U.S. Pat. No. 8,053,240, and entitled "Formulations for Imparting Traceability and/or Tractability to One or More Chemicals," which claims priority to U.S. Provisional Patent Application No. 61/200,571 filed Dec. 1, 2008 and entitled "Formulations for Imparting Traceability and/or Tractability to One or More Chemicals," the disclosures of which are hereby incorporated herein by reference in their entireties.

FIELD OF THE INVENTION

The invention relates to formulations that can be used to render chemicals easier to identify upon application to a surface. In one embodiment, the present invention relates to formulations designed to render herbicides, fungicides, pesticides, insecticides and/or phytotoxins easier to identify upon application to one or more types of vegetation. In another embodiment, the present invention relates to formulations designed to render water-soluble herbicides, fungicides, pesticides, insecticides and/or phytotoxins easier to identify upon application to one or more types of vegetation.

BACKGROUND OF THE INVENTION

A wide variety of chemicals are used every day. In most instances, particularly home uses, it is often difficult to ascertain exactly where a chemical has been applied. One such non-limiting example is when a herbicide or phytotoxin is used on vegetation. Due in part to the fact that most forms of vegetation are green it is often very difficult to determine where the herbicide or phytotoxin has been applied. More particularly, the use of water-soluble herbicides such as those sold under the Roundup® umbrella are difficult to track once applied to vegetation. While not wishing to be bound to any one theory, it is believed that this is due in large part to the use of a water-soluble herbicide composition at a relatively low concentration that imparts little to no colorization, or traceability.

Given this, there is a need in the art for chemical formulations that are designed to yield traceable formulations upon application to one or more surfaces (e.g., vegetation).

SUMMARY OF THE INVENTION

The invention relates to formulations that can be used to render chemicals easier to identify upon application to a surface. In one embodiment, the present invention relates to formulations designed to render herbicides, fungicides, pesticides, insecticides and/or phytotoxins easier to identify upon application to one or more types of vegetation. In another embodiment, the present invention relates to formulations designed to render water-soluble herbicides, fungicides, pesticides, insecticides and/or phytotoxins easier to identify upon application to one or more types of vegetation.

In one embodiment, the present invention relates to a formulation designed to impart "traceability" and/or trackability to a chemical as disclosed and discussed herein.

In another embodiment, the present invention relates to a formulation designed to impart "traceability" and/or trackability to one or more herbicides, fungicides, pesticides, insecticides and/or phytotoxins.

In still another embodiment, the present invention relates to a formulation designed to impart "traceability" and/or trackability to one or more water-based herbicides, fungicides, pesticides, insecticides and/or phytotoxins.

In still yet another embodiment, the present invention relates to a talcum powder-based formulation designed to impart "traceability" and/or trackability to one or more water-based herbicides, fungicides, pesticides, insecticides and/or phytotoxins.

In still yet another embodiment, the present invention relates to a talcum powder-based formulation designed to impart "traceability" and/or trackability to one or more water-based glyphosate-based herbicides.

In still yet another embodiment, the present invention is directed to a traceable, or trackable, chemical formulation comprising: an active portion comprising: about 0.1 weight percent to about 99 weight percent of at least one active ingredient; and about 99.9 weight percent to about 1 weight percent of at least one solvent; and about 0.1 weight percent to about 200 weight percent of at least one color-imparting compound based on the weight amount of the active portion.

In still yet another embodiment, the present invention is directed to a traceable, or trackable, chemical formulation comprising: an active portion comprising: about 0.1 weight percent to about 99 weight percent of at least one active herbicide ingredient; and about 99.9 weight percent to about 1 weight percent of at least one solvent; and about 0.1 weight percent to about 200 weight percent of at least one color-imparting compound based on the weight amount of the active portion.

In still yet another embodiment, the present invention is directed to a traceable, or trackable, chemical formulation comprising: an active portion comprising: about 0.1 weight percent to about 99 weight percent of at least one active glyphosate-based herbicide ingredient; and about 99.9 weight percent to about 1 weight percent of at least one solvent; and about 0.1 weight percent to about 200 weight percent of at least one color-imparting compound based on the weight amount of the active portion, wherein the at least one color-imparting compound is selected from talcum powder or graphite powder.

DETAILED DESCRIPTION OF THE INVENTION

The invention relates to formulations that can be used to render chemicals easier to identify upon application to a surface. In one embodiment, the present invention relates to formulations designed to render herbicides, fungicides, pesticides, insecticides and/or phytotoxins easier to identify upon application to one or more types of vegetation. In another embodiment, the present invention relates to formulations designed to render water-soluble herbicides, fungicides, pesticides, insecticides and/or phytotoxins easier to identify upon application to one or more types of vegetation.

More specifically, in one embodiment the present invention is directed to one or more formulations that can be added to one or more herbicides, fungicides, pesticides, insecticides and/or phytotoxins to yield a modified herbicide, fungicide, pesticide, insecticide and/or phytotoxin that is easier to identify upon application to a given surface. In another embodiment the present invention is directed to one or more formulations that can be added to one or more water-soluble herbicides, fungicides, pesticides, insecticides and/or phytotoxins to yield a modified herbicide, fungicide, pesticide, insecticide and/or phytotoxin that is easier to identify upon application to a given surface. In all embodiments, such application surfaces include, but are not limited to, cement, tile, flooring, wood, dirt, vegetation, linoleum, mulch, grass, or a combination of two or more thereof.

In still another embodiment, the formulations of the present invention are non-reactive. That is, in this embodiment, the formulations of the present invention do not react with the one or more herbicides, fungicides, pesticides, insecticides and/or phytotoxins to which they are added. It should be noted that the time at which the formulations of the present invention are added to the one or more such herbicides, fungicides, pesticides, insecticides and/or phytotoxins to be rendered "more visible" is not critical. In one embodiment, the formulations of the present invention can be added during the production process of such herbicides, fungicides, pesticides, insecticides and/or phytotoxins so long as the addition of the formulations of the present invention do not interfere with the production process or effectiveness of the herbicide, fungicide, pesticide, insecticide and/or phytotoxin portion of the final composition.

In another embodiment, the formulations of the present invention can be added to one or more herbicides, fungicides, pesticides, insecticides and/or phytotoxins during packaging, mixing (be it mixing for production or application), or any post production point. In one instance, the formulations of the present invention can be packaged separately and added during the mixing process just prior to application. In this embodiment, both the herbicide, fungicide, pesticide, insecticide and/or phytotoxin (whether in ready-to-use or concentrate form) and the formulation of the present invention are added to an appropriate container (e.g., a pump sprayer) and mixed together. In some embodiments, it may be desirable, or necessary, to add water to such mixture. In some embodiments, this water is necessary to achieve the proper concentration of the herbicide, fungicide, pesticide, insecticide and/or phytotoxin.

Turning now to the formulations of the present invention that are designed to impart "traceability," or trackability, to a wide variety of chemicals including, but not limited to, herbicides, fungicides, pesticides, insecticides and/or phytotoxins, in one embodiment such formulations are non-reactive with the base chemical to which they are added. In another embodiment, the formulations of the present invention are non-toxic. In still another embodiment, the formulations of the present invention do not interfere with the functionality of the one or more chemicals, to which they are added, upon application to a desired surface. In still yet another embodiment, the formulations of the present invention do not decrease the effectiveness of the one or more chemicals, to which they are added, upon application to the desired surface.

In one embodiment, the formulations of the present invention are comprised of one or more powdered, dry, or solid color-imparting compounds. In one embodiment, such powdered, dry, or solid color-imparting compounds are soluble in the chemical composition to which they are being added. In another embodiment, such powdered, dry, or solid color-imparting compounds are not soluble in the chemical composition to which they are being added.

In one embodiment, the powdered, dry, or solid color-imparting compounds include, but are not limited to, powdered colored dyes, colorants, natural colored mineral powders (e.g., talcum powder, graphite), or combinations of two or more thereof. The color of the powdered, dry, or solid color-imparting compounds of the present invention is not critical so long as the color is visible when applied to the desired surface. For example, with vegetation a color like white is useful as it more readily masks the green color of vegetation and permits for easier visual identification, trackability and/or traceability of the chemical in question. However, any color can be used and the present invention is not limited to any one color, or any one color-application surface combination.

In the case where powdered, dry, or solid color-imparting compounds are used in the formulations of the present invention, the particle geometry of such powders is not critical. As such, any particle geometry can be used. Such particle geometries include, but are not limited to, needles, spheres, platelets, irregular shapes, or combinations of two or more thereof. In another embodiment, where sprayability of a chemical compound is desired, the formulation of the present invention can have particles that are spherical in shape.

In one instance, the size of the particles and/or the average particle diameter of the powdered, dry, or solid color-imparting compounds of the present invention is not critical. In one embodiment, the size of the particles and/or the average particle diameter is in the range of about 1 nanometer to about 1 millimeter, or from about 5 nanometers to about 0.75 millimeters, or from about 10 nanometers to about 0.5 millimeters, or from about 25 nanometers to about 0.35 millimeters, or from about 50 nanometers to about 0.25 millimeters, or from about 100 nanometers to about 0.1 millimeters, or from about 200 nanometers to about 0.075 millimeters, or from about 300 nanometers to about 0.05 millimeters, or from about 400 nanometers to about 0.025 millimeters, or from about 500 nanometers to about 0.01 millimeters, or from about 600 nanometers to about 0.0075 millimeters, or from about 700 nanometers to about 0.005 millimeters, or from about 800 nanometers to about 0.0035 millimeters, or from about 800 nanometers to about 0.0025 millimeters, or even from about 900 nanometers to about 1 micron. Here, as well as elsewhere in the specification and claims, individual numerical values, or limits, can be combined to form additional non-disclosed and/or non-stated ranges.

In another embodiment, the size of the particles and/or the average particle diameter is in the range of about 1 micron to about 1 millimeter, or from about 5 microns to about 0.5 millimeters, or from about 10 microns to about 0.25 millimeters, or from about 25 microns to about 0.1 millimeters, or even from about 50 microns to about 75 microns. Here, as well as elsewhere in the specification and claims, individual numerical values, or limits, can be combined to form additional non-disclosed and/or non-stated ranges.

In still another embodiment, the size of the particles and/or the average particle diameter of the powdered, dry, or solid color-imparting compounds of the present invention is in the range of about 1 nanometer to about 1 micron, or from about 5 nanometers to about 0.5 microns, or from about 10 nanometers to about 0.25 microns, or from about 25 nanometers to about 0.1 microns, or even from about 50 nanometers to about 75 nanometers. Here, as well as elsewhere in the specification and claims, individual numerical values, or limits, can be combined to form additional non-disclosed and/or non-stated ranges.

As is noted above, the size of the particles of the powdered, dry, or solid color-imparting compounds, the average particle diameter of the powdered, dry, or solid color-imparting compounds, and/or the particle geometry of the powdered, dry, or solid color-imparting compounds of the present invention is not critical so long as the resulting mixture of the one or more powdered, dry, or solid color-imparting compounds and the chemical (e.g., a herbicide, fungicide, pesticide, insecticide and/or phytotoxin) to be applied can still be applied in any desired and/or suitable manner (e.g., spraying, misting, etc.). In the case of where the chemical in question is to be applied via spraying (e.g., with a pump sprayer, hand sprayer, mechanical sprayer, etc.), the size of the particles, the average particle diameter of the particles and/or the particle geometry of the particles of the one or more powdered, dry, or solid color-imparting compounds of the present invention should not detrimentally affect the sprayability of such chemical. As would be apparent to those of skill in the art, the size of the particles, the average particle diameter of the particles and/or the particle geometry of the particles of the one or more powdered, dry, or solid color-imparting compounds of the present invention are selected depending upon the type of application equipment being utilized. In one embodiment, this would include, among other considerations that would be apparent to those of skill in the art, the size of the spray nozzle, the supply lines in the spraying equipment (if applicable) and any other points of flow constriction that might exist.

In another embodiment, the amount of the powdered, dry, or solid color-imparting compounds added to a liquid chemical (e.g., a herbicide, fungicide, pesticide, insecticide and/or phytotoxin) to impart "traceability," or trackability thereto is not critical so long as the chemical can still be applied in a suitable manner. In the case where the chemical in question is to be applied via spraying (e.g., with a pump sprayer), the amount of the powdered, dry, or solid color-imparting compound added thereto should not detrimentally affect the sprayability of such chemical. As would be apparent to those of skill in the art, the amount of the powdered, dry, or solid color-imparting compound that might detrimentally affect the sprayability of a chemical depends on the spraying method and/or spraying equipment used.

In one embodiment, the amount of the powdered, dry, or solid color-imparting compounds added to a liquid chemical (e.g., a herbicide, fungicide, pesticide, insecticide and/or phytotoxin) to impart "traceability," or trackability thereto is in the range of about 0.1 weight percent to about 200 weight percent based on the weight of the ready-to-apply chemical. In still another embodiment, the amount of the powdered, dry, or solid color-imparting compounds added to a liquid chemical (e.g., a herbicide, fungicide, pesticide, insecticide and/or phytotoxin) to impart "traceability," or trackability thereto is in the range of about 1 weight percent to about 150 weight percent, or from about 2.5 weight percent to about 100 weight percent, or from about 5 weight percent to about 80 weight percent, or from about 7.5 weight percent to about 70 weight percent, or from about 10 weight percent to about 60 weight percent, or from about 12.5 weight percent to about 50 weight percent, or from about 15 weight percent to about 40 weight percent, or from about 20 weight percent to about 30 weight percent, or even from about 25 weight percent to about 27.5 weight percent based on the weight of the ready-to-apply chemical. Here, as well as elsewhere in the specification and claims, individual numerical values, or limits, can be combined to form additional non-disclosed and/or non-stated ranges.

In the case where the powdered, dry, or solid color-imparting compounds are soluble in the liquid chemical, the amount added thereto should not exceed the amount that is soluble in such a liquid chemical. In the case where the powdered, dry, or solid color-imparting compounds are not soluble in the liquid chemical, the amount added thereto should, as is discussed above, not detrimentally affect the applicability, sprayability, and/or efficacy of such a liquid chemical.

In another embodiment, the color-imparting compounds of the present invention are liquid color compounds. Such compounds (e.g., liquid colorants or dyes) can be water-based, organic-based, or oil-based compounds. In still another embodiment, the color-imparting compounds of the present invention are encapsulated color-imparting compounds. Such color-imparting compounds include, but are not limited to, powdered colored dyes, colorants, natural colored mineral powders (e.g., talcum powder, graphite), or combinations of two or more thereof. In the case of the encapsulated color compounds, the color portion thereof can be encapsulated with any suitable material. Suitable materials include, but are not limited to, polymers, glass, silica, or combinations of two or more thereof.

In one embodiment, the amount of the liquid color-imparting compounds added to a liquid chemical (e.g., a herbicide, fungicide, pesticide, insecticide and/or phytotoxin) to impart "traceability," or trackability thereto is not critical so long the chemical can still be applied in a suitable manner. In the case of where the chemical in question is to be applied via spraying (e.g., with a pump sprayer), the amount of the liquid color-imparting compound added thereto should not detrimentally affect the sprayability of such chemical. As would be apparent to those of skill in the art, the amount of the liquid color-imparting compound that might detrimentally affect the sprayability of a chemical depends on the spraying method and/or spraying equipment used.

In one embodiment, the amount of the liquid color-imparting compounds added to a liquid chemical (e.g., a herbicide, fungicide, pesticide, insecticide and/or phytotoxin) to impart "traceability," or trackability thereto is in the range of about 0.1 weight percent to about 200 weight percent based on the weight of the ready-to-apply chemical. In still another embodiment, the amount of the powdered color-imparting compounds added to a liquid chemical (e.g., a herbicide, fungicide, pesticide, insecticide and/or phytotoxin) to impart "traceability," or trackability thereto is in the range of about 1 weight percent to about 150 weight percent, or from about 2.5 weight percent to about 100 weight percent, or from about 5 weight percent to about 80 weight percent, or from about 7.5 weight percent to about 70 weight percent, or from about 10 weight percent to about 60 weight percent, or from about 12.5 weight percent to about 50 weight percent, or from about 15 weight percent to about 40 weight percent, or from about 20 weight percent to about 30 weight percent, or even from about 25 weight percent to about 27.5 weight percent based on the weight of the ready-to-apply chemical. Here, as well as elsewhere in the specification and claims, individual numerical values, or limits, can be combined to form additional non-disclosed and/or non-stated ranges.

In still yet another embodiment, the formulations of the present invention that are designed to impart "traceability," or trackability, to a wide variety of chemicals including, but not limited to, herbicides, fungicides, pesticides, insecticides and/or phytotoxins, can either be in a dry or powdered form, can be one or more dry or powder color-imparting compounds that are combined with one or more liquids. Such liquids include, but are not limited to, water, alcohols, organic solvents, oil, or suitable combinations of two or more thereof. In one embodiment, the solvent used is either environmentally-friendly, environmentally-benign, non-toxic, or any combination thereof.

In still yet another embodiment, the formulations of the present invention that are designed to impart "traceability," or trackability, to a wide variety of chemicals including, but not limited to, herbicides, fungicides, pesticides, insecticides and/or phytotoxins, can further include one or more additional additives. Such additional additives include, but are not limited to, surfactants, viscosity modifiers, anti-coagulation agents, anti-settling agents, dispersants, antifreeze, or any suitable combination of two or more thereof. In one embodiment, the one or more additional additives are present in any suitable amount so long as their presence does not detrimentally affect the applicability, sprayability, and/or efficacy of the one or more chemicals (i.e., active ingredients) to be applied. In another embodiment, the compositions of the present invention can contain up to about 10 percent by weight of the one or more additional additives, or up to about 7.5 percent by weight of the one or more additional additives, or up to about 5 percent by weight of the one or more additional additives, or up to about 2.5 percent by weight of the one or more additional additives, or up to about 1 percent by weight of the one or more additional additives, or up to about 0.5 percent by weight of the one or more additional additives, or even up to about 0.1 percent by weight of the one or more additional additives based on the weight amount of the one or more chemicals to be applied, the one or more color-imparting compounds of the present invention and, if necessary or desirable, one or more solvents present.

In another embodiment, the compositions according to the present invention are free from any of the abovementioned additives and only contain the one or more chemicals to be applied, the one or more color-imparting compounds of the present invention and, if necessary or desirable, one or more solvents. By "free of" it is meant that the compositions of the present invention have less than about 2 weight percent of the one or more additional additives, less than about 1 weight percent of the one or more additional additives, less than about 0.5 weight percent of the one or more additional additives, less than about 0.1 weight percent of the one or more additional additives, less than about 0.01 weight percent of the one or more additional additives, less than about 0.001 weight percent of the one or more additional additives, or even zero weight percent of the one or more additional additives based on the weight amount of the one or more chemicals to be applied, the one or more color-imparting compounds of the present invention and, if necessary or desirable, one or more solvents present.

In still another embodiment, the formulations of the present invention are designed to impart "traceability," or trackability to a broad spectrum of vegetation herbicides such as glyphosate, its salts, its esters, or some other water-soluble form thereof. Such chemicals are sold under various brand names including, but not limited to, Roundup®. A large number of United States Patents deal with suitable glyphosate-based, glyphosate-derived, herbicides. Examples thereof include, but are not limited to, U.S. Pat. Nos. 3,799,758; 5,703,015; 6,063,733; 6,121,199; 6,121,200; and 7,135,437. All of these patents are incorporated herein by reference in their entireties. Additional glyphosate formulations of interest are disclosed in European Patent No. 290416, which is incorporated herein by reference in its entirety.

In this embodiment since the application of Roundup® to green vegetation is difficult to ascertain a colorizing compound is added thereto. In one instance a suitable amount of talcum powder is added to a sprayer containing a desired Roundup® mixture so that upon application it is possible to track and/or ascertain where the Roundup® has been applied. In one embodiment, the amount of talcum powder to impart "traceability," or trackability to the Roundup® is in the range of about 0.1 weight percent to about 200 weight percent based on the weight of the ready-to-apply chemical, or from about 0.5 weight percent to about 100 weight percent talcum based on the weight of the ready-to-apply chemical, or even from about 1 weight percent to about 75 weight percent talcum based on the weight of the ready-to-apply chemical. Here, as well as elsewhere in the specification and claims, individual numerical values, or limits, can be combined to form additional non-disclosed and/or non-stated ranges.

In another embodiment, the amount of talcum powder to impart "traceability," or trackability to the Roundup® is in one of the ranges detailed above. In still another embodiment, the amount of talcum powder to impart "traceability," or trackability to the Roundup® is in the range of about 0.1 weight percent to about 50 weight percent, or from about 0.5 weight percent to about 45 weight percent, or from about 1 weight percent to about 40 weight percent, or from about 2.5 weight percent to about 35 weight percent, or from about 5 weight percent to about 30 weight percent, or from about 10 weight percent to about 25 weight percent, or from about 12.5 weight percent to about 20 weight percent, or even from about 15 weight percent to about 17.5 weight percent based on the weight of the ready-to-apply chemical. Here, as well as elsewhere in the specification and claims, individual numerical values, or limits, can be combined to form additional non-disclosed and/or non-stated ranges.

In one embodiment, the present invention is a combination of one or more active ingredients (e.g., herbicides, fungicides, pesticides, insecticides and/or phytotoxins) with one or more suitable solvents. Suitable solvents include, but are not limited to, water, alcohol (e.g., alkyl alcohols such as ethanol, etc.), or mixtures of two or more thereof. In another embodiment, the one or more active ingredients (e.g., herbicides, fungicides, pesticides, insecticides and/or phytotoxins) can be either water-based or oil-based active ingredients.

In one embodiment, the combination of the one or more active ingredients (e.g., herbicides, fungicides, pesticides, insecticides and/or phytotoxins) with the one or more suitable solvents can be in the form of a mixture or an emulsion thereby yielding the aforementioned liquid chemical. It should be noted that the present invention is not limited to active ingredients that are in liquid form. Rather, any liquid or solid form of active ingredient can be utilized so long as the active ingredient can be put into solution for spray application. Upon the addition of the one or more color-imparting compounds of the present invention, a mixture, a multiple component emulsion, or a suspension can be achieved. In one instance, as is noted above, the one or more color-imparting compounds of the present invention are insoluble in the solvent system used in combination with the one or more desired active ingredients. In this case, the one or more color-imparting compounds of the present invention may, or may not, form a suspension. In one embodiment, a suitable anti-settling agent and/or anti-coagulation agent can also be added to the mixture of the one or more active ingredients, the one or more solvents, and the one or more color-imparting compounds of the present invention.

In another instance, as is noted above, the one or more color-imparting compounds of the present invention are soluble in the solvent system used in combination with the one or more desired active ingredients. In this case, the one or more color-imparting compounds of the present invention may, or may not, form an emulsion with the solvent used. In still another instance, as is noted above, the one or more color-imparting compounds of the present invention are in liquid form and are either soluble or insoluble in the solvent system used in combination with the one or more desired active ingredients. In this case, when the one or more color-imparting compounds of the present invention are insoluble liquids, a suitable co-solvent can be utilized to achieve a more homogenous mixture of the liquid color-imparting compounds of the present invention.

Regarding the active portion of the present invention as described above, this active portion can be any suitable combination of at least one active ingredient with at least one solvent. The amount of the at least one active ingredient to the at least one solvent is not critical as long as the final concentration of the at least one active ingredient is suitable for its intended application. Suitable concentrations will vary depending upon the nature of the at least one active ingredient, the intended application for the final product, and/or the intended use for the final product.

In one embodiment, the amount of the at least one active ingredient to the amount of the at least one solvent is about 0.1 weight percent of the at least one active ingredient to about 99.9 weight percent of the at least one solvent, or from about 0.5 weight percent of the at least one active ingredient to about 99.5 weight percent of the at least one solvent, or from about 1 weight percent of the at least one active ingredient to about 99 weight percent of the at least one solvent, or from about 1.5 weight percent of the at least one active ingredient to about 98.5 weight percent of the at least one solvent, or from about 2.5 weight percent of the at least one active ingredient to about 97.5 weight percent of the at least one solvent, or from about 5 weight percent of the at least one active ingredient to about 95 weight percent of the at least one solvent, or from about 7.5 weight percent of the at least one active ingredient to about 92.5 weight percent of the at least one solvent, or from about 10 weight percent of the at least one active ingredient to about 90 weight percent of the at least one solvent, or from about 12.5 weight percent of the at least one active ingredient to about 87.5 weight percent of the at least one solvent, or from about 15 weight percent of the at least one active ingredient to about 85 weight percent of the at least one solvent, or from about 20 weight percent of the at least one active ingredient to about 80 weight percent of the at least one solvent, or from about 25 weight percent of the at least one active ingredient to about 75 weight percent of the at least one solvent, or from about 30 weight percent of the at least one active ingredient to about 70 weight percent of the at least one solvent, or from about 40 weight percent of the at least one active ingredient to about 60 weight percent of the at least one solvent, or from about 45 weight percent of the at least one active ingredient to about 55 weight percent of the at least one solvent, or even from about 50 weight percent of the at least one active ingredient to about 50 weight percent of the at least one solvent.

In one embodiment, the amount of the at least one active ingredient to the amount of the at least one solvent is about 99 weight percent of the at least one active ingredient to about 1 weight percent of the at least one solvent, or from about 97.5 weight percent of the at least one active ingredient to about 2.5 weight percent of the at least one solvent, or from about 95 weight percent of the at least one active ingredient to about 5 weight percent of the at least one solvent, or from about 90 weight percent of the at least one active ingredient to about 10 weight percent of the at least one solvent, or from about 85 weight percent of the at least one active ingredient to about 15 weight percent of the at least one solvent, or from about 80 weight percent of the at least one active ingredient to about 20 weight percent of the at least one solvent, or from about 75 weight percent of the at least one active ingredient to about 25 weight percent of the at least one solvent, or from about 70 weight percent of the at least one active ingredient to about 30 weight percent of the at least one solvent, or from about 65 weight percent of the at least one active ingredient to about 35 weight percent of the at least one solvent, or from about 60 weight percent of the at least one active ingredient to about 40 weight percent of the at least one solvent, or from about 55 weight percent of the at least one active ingredient to about 45 weight percent of the at least one solvent, or even from about 50 weight percent of the at least one active ingredient to about 50 weight percent of the at least one solvent.

The following are exemplary formulations in accordance with the present invention. However, they are exemplary in nature and the present invention is not limited thereto. Rather, the present invention is to be broadly construed in accordance with the disclosure contained herein.

In one embodiment, the present invention is directed to a traceable, or trackable, chemical formulation comprising: an active portion comprising: about 0.1 weight percent to about 99 weight percent of at least one active ingredient; and about 99.9 weight percent to about 1 weight percent of at least one solvent; and about 0.1 weight percent to about 200 weight percent of at least one color-imparting compound based on the weight amount of the active portion.

In another embodiment, the present invention is directed to a traceable, or trackable, chemical formulation comprising: an active portion comprising: about 0.1 weight percent to about 99 weight percent of at least one active herbicide ingredient; and about 99.9 weight percent to about 1 weight percent of at least one solvent; and about 0.1 weight percent to about 200 weight percent of at least one color-imparting compound based on the weight amount of the active portion.

In still another embodiment, the present invention is directed to a traceable, or trackable, chemical formulation comprising: an active portion comprising: about 0.1 weight percent to about 99 weight percent of at least one active glyphosate-based herbicide ingredient; and about 99.9 weight percent to about 1 weight percent of at least one solvent; and about 0.1 weight percent to about 200 weight percent of at least one color-imparting compound based on the weight amount of the active portion, wherein the at least one color-imparting compound is selected from talcum powder or graphite powder.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A traceable, or trackable, chemical formulation comprising at least one fungicide, pesticide, insecticide and/or phytotoxin compound chemical formulation, the at least one fungicide, pesticide, insecticide and/or phytotoxin chemical formulation comprising:
   an active portion comprising at least one chemical fungicide, pesticide, insecticide and/or phytotoxin compound, wherein the active portion is soluble in an aqueous-based solvent; and
   at least one color-imparting compound, wherein the at least one color-imparting compound is insoluble in the aqueous-based solvent,
   wherein at least one color-imparting compound is selected from talcum powder or graphite powder.

2. The chemical formulation of claim 1, wherein the at least one chemical fungicide, pesticide, insecticide and/or phytotoxin compound in the active portion is present in the range of about 0.1 weight percent to about 90 weight percent and the aqueous-based solvent is present in the active portion in the range of about 99.9 weight percent to about 10 weight percent.

3. The chemical formulation of claim 1, wherein the at least one chemical fungicide, pesticide, insecticide and/or phytotoxin compound in the active portion is present in the range of about 15 weight percent to about 85 weight percent and the aqueous-based solvent is present in the active portion in the range of about 85 weight percent to about 15 weight percent.

4. The chemical formulation of claim 1, wherein the amount of the at least one color-imparting compound is in the range of about 0.1 weight percent to about 50 weight percent based on the weight of the ready-to-apply chemical formulation.

5. The chemical formulation of claim 1, wherein the amount of the at least one color-imparting compound is in the range of about 0.5 weight percent to about 45 weight percent based on the weight of the ready-to-apply chemical formulation.

6. The chemical formulation of claim 1, wherein the amount of the at least one color-imparting compound is in the range of about 1 weight percent to about 40 weight percent based on the weight amount of the active portion.

7. The chemical formulation of claim 1, wherein the amount of the at least one color-imparting compound is in the range of about 2.5 weight percent to about 35 weight percent based on the weight amount of the active portion.

8. The chemical formulation of claim 1, wherein the amount of the at least one color-imparting compound is in the range of about 5 weight percent to about 30 weight percent based on the weight amount of the active portion.

9. A traceable, or trackable, chemical formulation comprising at least one fungicide, pesticide, insecticide and/or phytotoxin chemical formulation, the at least one fungicide, pesticide, insecticide and/or phytotoxin chemical formulation comprising:
    an active portion comprising at least one chemical fungicide, pesticide, insecticide and/or phytotoxin compound, wherein the active portion is soluble in an aqueous-based solvent; and
    at least one color-imparting compound, wherein the at least one color-imparting compound is insoluble in the aqueous-based solvent,
    wherein the at least one color-imparting compound is a powdered, dry or solid color-imparting compound.

10. The chemical formulation of claim 9, wherein the at least one color-imparting compound is selected from powdered colored dyes, colorants, natural colored mineral powders, or combinations of two or more thereof.

11. The chemical formulation of claim 10, wherein the at least one color-imparting compound is selected from talcum powder or graphite powder.

12. The chemical formulation of claim 9, wherein the at least one chemical fungicide, pesticide, insecticide and/or phytotoxin compound in the active portion is present in the range of about 0.1 weight percent to about 90 weight percent and the aqueous-based solvent is present in the active portion in the range of about 99.9 weight percent to about 10 weight percent.

13. The chemical formulation of claim 9, wherein the at least one chemical fungicide, pesticide, insecticide and/or phytotoxin compound in the active portion is present in the range of about 15 weight percent to about 85 weight percent and the aqueous-based solvent is present in the active portion in the range of about 85 weight percent to about 15 weight percent.

14. The chemical formulation of claim 9, wherein the amount of the at least one color-imparting compound is in the range of about 0.1 weight percent to about 50 weight percent based on the weight of the ready-to-apply chemical formulation.

15. The chemical formulation of claim 9, wherein the amount of the at least one color-imparting compound is in the range of about 0.5 weight percent to about 45 weight percent based on the weight of the ready-to-apply chemical formulation.

16. A traceable, or trackable, chemical formulation comprising at least one fungicide, pesticide and/or insecticide chemical formulation, the at least one fungicide, pesticide and/or insecticide chemical formulation comprising:
    an active portion comprising at least one chemical fungicide, pesticide and/or insecticide compound, wherein the active portion is soluble in an aqueous-based solvent; and
    at least one color-imparting compound, wherein the at least one color-imparting compound is insoluble in the aqueous-based solvent,
    wherein the at least one color-imparting compound is a powdered, dry or solid mineral color-imparting compound.

17. The chemical formulation of claim 16, wherein the at least one color-imparting compound is selected from talcum powder or graphite powder.

18. The chemical formulation of claim 16, wherein the amount of the at least one color-imparting compound is in the range of about 0.1 weight percent to about 50 weight percent based on the weight of the ready-to-apply chemical formulation.

19. The chemical formulation of claim 16, wherein the amount of the at least one color-imparting compound is in the range of about 0.5 weight percent to about 45 weight percent based on the weight of the ready-to-apply chemical formulation.

20. The chemical formulation of claim 16, wherein the at least one active chemical in the active portion is an insecticide.

* * * * *